United States Patent [19]

Jahn et al.

[11] Patent Number: 4,797,606
[45] Date of Patent: Jan. 10, 1989

[54] MEASURING DEVICE FOR THE MEASUREMENT OF THE DEFORMABILITY OF RED BLOOD CORPUSCLES

[75] Inventors: Helmut Jahn, Mainz; Waldemar Karger, Kelkheim, both of Fed. Rep. of Germany

[73] Assignee: Hoechst Aktiengesellschaft, Frankfurt am Main, Fed. Rep. of Germany

[21] Appl. No.: 876,165

[22] Filed: Jun. 19, 1986

[30] Foreign Application Priority Data

Jun. 21, 1985 [DE] Fed. Rep. of Germany ....... 3522186

[51] Int. Cl.$^4$ ............................................. G01N 27/02
[52] U.S. Cl. .................................... 324/71.1; 324/71.4
[58] Field of Search ................. 324/71.1, 71.4; 377/11, 377/12; 128/734

[56] References Cited

U.S. PATENT DOCUMENTS 3,783,247  1/1974  Klein et al. ........................... 377/11
3,812,425  5/1974  Miller ................................. 324/71.1
4,220,916  9/1980  Zimmermann et al. ........... 324/71 R
4,521,729  6/1985  Kiesewetter et al. .............. 324/71.1

Primary Examiner—Reinhard J. Eisenzopf
Assistant Examiner—Jack B. Harvey
Attorney, Agent, or Firm—Finnegan, Henderson, Farabow, Garrett, & Dunner

[57] ABSTRACT

The deformability measurement chamber is subdivided by a foil into two chamber spaces. The foil has a passage opening, the diameter of which is smaller than the diameter, at rest, of a red blood corpuscle. A static pressure gradient exists between the two chamber spaces, so that a flow takes place from one chamber space to the other. In the region of the passage opening there is situated on each side of the foil an electrode, which is connected to an alternating voltage source. In order to achieve a measurement signal which is approximately one order of magnitude greater, at a given alternating voltage frequency, a current-measuring operational amplifier is disposed in the connecton of one electrode to the voltage source.

5 Claims, 2 Drawing Sheets

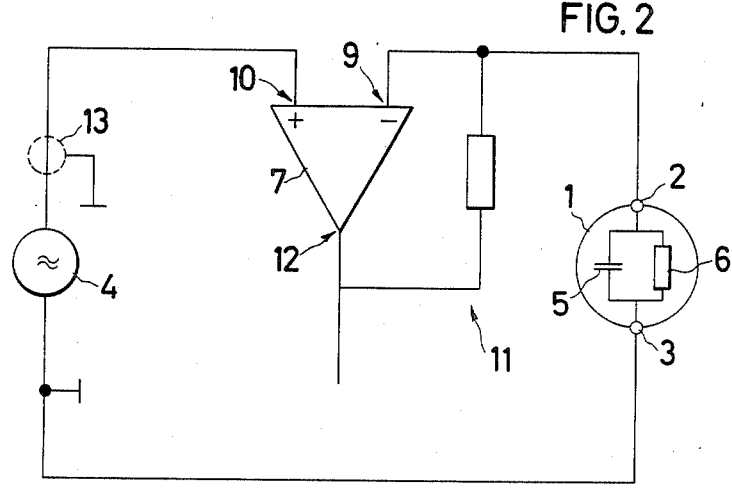
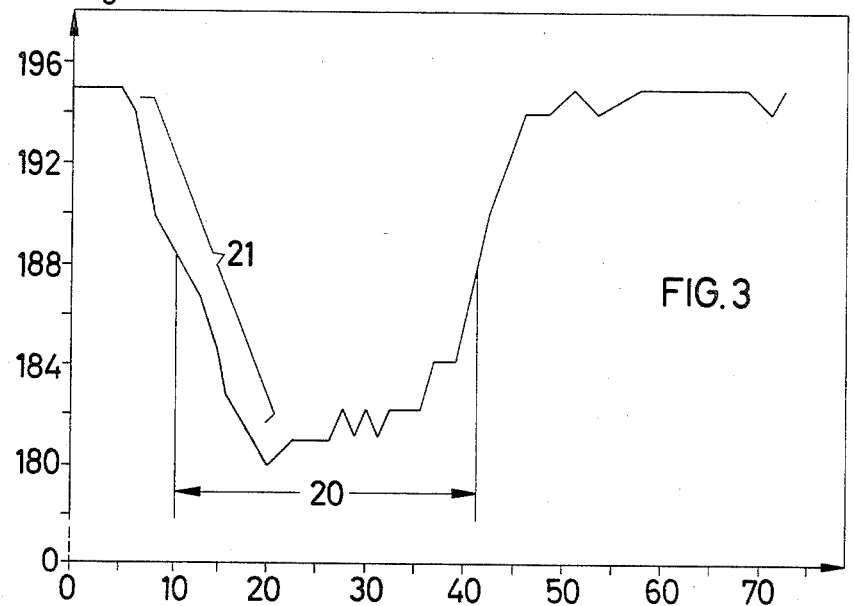

MEASURING DEVICE FOR THE MEASUREMENT OF THE DEFORMABILITY OF RED BLOOD CORPUSCLES

BACKGROUND OF THE INVENTION

1. Field of the Invention

The invention relates to a measuring device for the measurement of the deformability of red blood corpuscles, erythrocytes, which device comprises a measurement chamber, which is subdivided by a foil into two chamber spaces, the foil having a passage opening, the diameter of which is smaller than the diameter, at rest, of a red blood corpuscle, the chamber spaces being formed in such a manner that a pressure gradient comes into existence between the two chamber spaces and thus a flow takes place from one chamber space to the other, and at least one electrode being disposed on each of the two sides of the foil in the region of the opening, each respective electrode being connected to an alternating voltage source.

2. Description of the Prior Art

A measuring device of the kind mentioned is known according to German Patent Specification No. 3,215,719. In order to measure the deformability of the erythrocytes, one of the chamber spaces of the measurement chamber is filled with a mixture of buffer solution and complete blood, and the other with buffer solution. Since a hydrostatic pressure gradient is present because of the channel course, the erythrocytes are caused to pass through the opening in the foil. In this connection, the time which the individual erythrocytes require in order to pass through a single-aperture membrane serves as a measure of the deformability. In the course of the passage of the erythrocyte through the opening of the foil, the total electrical resistance of the measurement chamber changes. This change is recorded; it is a direct measure of the passage time. An alternating voltage is applied under high-resistance conditions to the electrodes situated on both sides of the opening, and the total resistance—which changes during the passage of the erythrocyte through the opening—of the measurement cell is recorded in the form of a change in voltage.

A disadvantage in the case of the measurement of an alternating voltage is that the foil itself represents a capacitor, so that, in addition, a parasitic capacitive resistance is connected in parallel with the ohmic resistance of the opening. To this there are also added parasitic shunt capacities. An increase in the frequency does indeed lead to increasing resolution of the transit times, but the value of the capacitive resistance decreases. This results in a change—which becomes progressively smaller with increasing measurement frequencies—of the measurement signal on passage of the erythrocytes through the opening in the foil, so that a costly electronic analysis system becomes necessary.

SUMMARY OF THE INVENTION

The invention is intended to provide a remedy in this connection. The object of the invention is accordingly to provide a measuring device for measurement of the deformability of red blood corpuscles, in which device a measurement signal which is approximately one order of magnitude greater is available at a given alternating voltage frequency.

The object is fulfilled in that a current-measuring device is disposed in the connection of one electrode to the alternating voltage source.

In a refinement of the invention, one of the electrodes can be connected to the alternating voltage source close to ground, and the current-measuring device can be disposed in this connection. As current-measuring device, an operational amplifier operating as an inverting amplifier, with an analog/digital converter connected behind the same, can be connected to the electrode. A filter and/or a peak value detector, for example a full-wave detector, can be connected before the analog/digital converter.

In the case of careful minimization of the ballast capacities in the measurement cell and the electrical connections, it is possible to achieve with the measuring device according to the invention a measurement signal which is approximately one order of magnitude greater. As a result of this, it is possible not only to determine the transit time but also, for the first time, to make statements concerning the qualitative graphical progression of the electrical measurement signal during the passage of the red blood corpuscle through the foil.

BRIEF DESCRIPTION OF THE DRAWINGS

The invention is explained in greater detail below, with reference to the figures. In the figures:

FIG. 2 shows a part of the electrical circuit of the measurement chamber, with an alternative arrangement of the operational amplifier, FIG. 3 shows the digitalized input signal for the microprocessor.

DESCRIPTION OF THE PREFERRED EMBODIMENT

Figure 1:
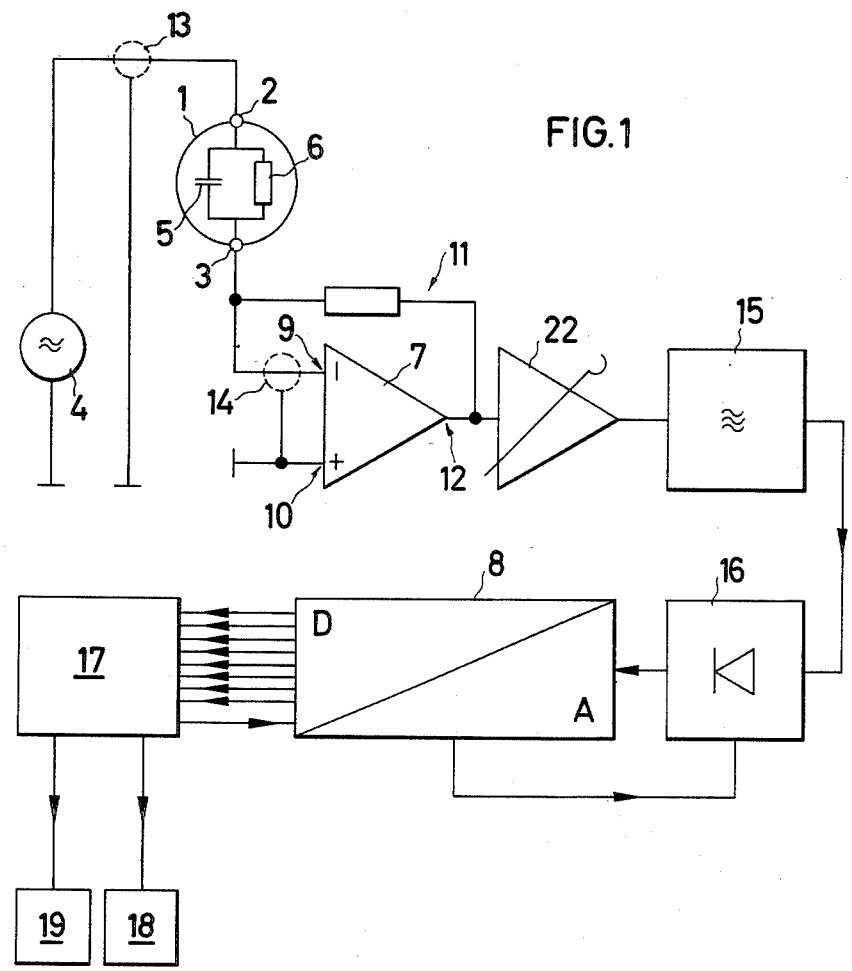
FIG. 1 shows the electrical circuit of the measuring device.

The measurement chamber of the measuring device, as is described for example in German Patent Specification No. 3,215,719, is subdivided by a foil into two chamber spaces. The foil has a passage opening, the diameter of which is smaller than the diameter, at rest, of a red blood corpuscle. The chamber spaces are formed in such a manner that a pressure gradient comes into existence between the two chamber spaces, and thus a flow takes place from one chamber space to the other, if a liquid containing the red blood corpuscles is situated in the chamber spaces. At least one electrode is disposed on each of the two sides of the foil in the region of the passage opening, each respective electrode being connected to an alternating voltage source 4. In FIGS. 1 and 2, the measurement chamber 1 is shown as an electrical equivalent circuit diagram. In this, the connections 2 and 3 stand for the electrodes, the unavoidable capacitive resistance 5 for the foil, and the ohmic resistance 6 for the conductive connecting path between the electrodes through the opening of the foil. In order to ascertain the resistance 5/6 and a change thereof, the electric current which flows in the measurement circuit including the alternating voltage source 4 and the measurement chamber 1 is directly measured. In principle, this can take place at any location within the measurement circuit. A current-measuring device is disposed in the connection between one of the electrodes 2, 3 and the alternating voltage source 4. The current-measuring device can consist of an operational amplifier 7 operating as an inverting amplifier. In this arrangement, the inverting input 9 of the amplifier is connected to the electrode 2 or 3, while the non-inverting input 10 is connected to the alternating voltage source 4 or to ground. The current is preferably measured at the cold conducting end of the measurement chamber. The inverting input 9 of the operational amplifier 7 is connected to the electrode 3 and creates a fictitious ground potential by regenerative coupling 11 of an equally large, oppositely directed current. By this means, an output voltage which is precisely proportional to the current is generated at the output 12 of the operational amplifier 7. In the course of the measurement of the current, virtually no voltage drop occurs between the electrode 3 and ground. As a result of the particular circuit technology, any connection—which would otherwise be harmful—of the measurement chamber 1 to ground is also of no significance. In principle, no parasitic currents are present in the measurement path, for which reason it is also possible to dispense with the use of an expensive instrumentation amplifier. Accordingly, relatively long, screened leads 13, 14 can be employed, without any problems, as feed line. As a result of the low-resistance conditions, both at the "hot" feed-in end (electrode 2) and also at the "cold" ground end (electrode 3) of the measurement chamber 1, interfering irradiative effects are to a large extent suppressed, even in the spectrum of the desired frequency. Possibly after suppression of further interfering effects by active filters 15, peak value detection can be undertaken by means of a peak value detector 16. The signal is subsequently fed, for further analysis, to an analog/digital converter 8, which has a resolving power sufficient to permit subsequent evaluation of the amplitude. The peak value detector 16 ensures that an adequate signal constancy is available to the analog/digital converter 8 during the period of conversion. In some cases, the use of a full-wave detector can be more favorable. By application of a micro-processor 17 following the analog/digital converter 8, it is possible without any change of the existing hardware construction, to undertake various analyses, which determine the information of relevance from the medical point of view from the measurement data. By means of analysis algorithms, a slowly drifting change of the measurement chamber current can be compensated, and it is possible to eliminate shorter interfering pulses which do not correspond to the characteristic progression of the passage of an erythrocyte. If necessary, an adjustable amplifier 22 can be connected behind the operational amplifier.

Finally, the total time requirement 20 (FIG. 3) for the single passage of an erythrocyte through the foil is determined, a statistic concerning this is computed, and the results are displayed on the display 18 and/or printed out by means of printer 19. Likewise, the detailed recording of especially important phases of the passages is made possible, e.g. the progress of the elongation phase 21 (FIG. 3) of the erythrocytes on entry into the opening of the foil.

We claim:

1. A measuring device for the measurement of the deformability of red blood corpuscles, which device comprises a measurement chamber, which is subdivided by a foil into two chamber spaces, the foil having a passage opening with a diameter smaller than the diameter, at rest, of a red corpuscle, said chamber spaces being formed such that a static pressure gradient comes into existence between said chamber spaces creating a flow from one chamber space to the other, and at least one electrode being disposed on each of the two sides of said foil in the region of the passage opening, each respective electrode being connected to an alternating voltage source, and an operational amplifier, having an inverting input and a non-inverting input functioning as a current-measuring device, said operational amplifier further including regenerative coupling means for creating a fictitious ground potential at said inverting input, said operational amplifier being disposed in the connection between one of said electrodes and said alternating voltage source, said one electrode being connected to said inverting input of said operational amplifier thereby disposing said one electrode closer to ground than the other of said electrodes.

2. The measuring device as claimed in claim 1, wherein said operational amplifier operates as an inverting amplifier, and wherein said measuring device further includes an analog/digital converter having an analog input terminal for receiving an analog signal from said operational amplifier.

3. The measuring device as claimed in claim 2, wherein a filter is disposed between said operational amplifier and said analog/digital converter.

4. The measuring device as claimed in claim 2, wherein a peak value detector is connected between said operational amplifier and said analog/digital converter.

5. The measuring device as claimed in claim 4, wherein said peak-value detector comprises a full-wave detector.

* * * * *